(12) United States Patent
Chuang et al.

(10) Patent No.: US 10,283,366 B2
(45) Date of Patent: May 7, 2019

(54) PASSIVATION OF NONLINEAR OPTICAL CRYSTALS

(71) Applicant: KLA-Tencor Corporation, Milpitas, CA (US)

(72) Inventors: Yung-Ho Chuang, Cupertino, CA (US); Vladimir Dribinski, Scotts Valley, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 0 days.

(21) Appl. No.: 15/284,231

(22) Filed: Oct. 3, 2016

(65) Prior Publication Data

US 2017/0025281 A1   Jan. 26, 2017

Related U.S. Application Data

(63) Continuation of application No. 15/010,331, filed on Jan. 29, 2016, now Pat. No. 9,459,215, which is a
(Continued)

(51) Int. Cl.
*H01L 21/30* (2006.01)
*C30B 29/10* (2006.01)
(Continued)

(52) U.S. Cl.
CPC .......... *H01L 21/3003* (2013.01); *C30B 29/10* (2013.01); *C30B 33/00* (2013.01);
(Continued)

(58) Field of Classification Search
CPC ...... H01L 21/3003; G01N 21/59; C30B 29/10
(Continued)

(56) References Cited

U.S. PATENT DOCUMENTS 3,966,300 A   6/1976   Bernsee
4,254,426 A * 3/1981   Pankove ................ H01L 21/56
                                                          136/258
(Continued)

FOREIGN PATENT DOCUMENTS

CN   1496478 A    5/2004
CN   101765900 A  6/2010
(Continued)

OTHER PUBLICATIONS

Yusuke Mori et al., New nonlinear optical crystal: Cesiom lithium borate, Applied Physics Letters 67, 1818 (1995); doi: 10.1063/1.115413, 4 pages, AIP Publishing.
(Continued)

*Primary Examiner* — Roy M Punnoose
(74) *Attorney, Agent, or Firm* — Suiter Swantz pc llo

(57) ABSTRACT

A laser system includes a nonlinear optical (NLO) crystal, wherein the NLO crystal is annealed within a selected temperature range. The NLO crystal is passivated with at least one of hydrogen, deuterium, a hydrogen-containing compound or a deuterium-containing compound to a selected passivation level. The system further includes at least one light source, wherein at least one light source is configured to generate light of a selected wavelength and at least one light source is configured to transmit light through the NLO crystal. The system further includes a crystal housing unit configured to house the NLO crystal.

15 Claims, 12 Drawing Sheets

Related U.S. Application Data continuation of application No. 13/488,635, filed on Jun. 5, 2012, now Pat. No. 9,250,178.

(60) Provisional application No. 61/544,425, filed on Oct. 7, 2011.

(51) Int. Cl.

| | |
|---|---|
| *C30B 33/00* | (2006.01) |
| *C30B 33/02* | (2006.01) |
| *G01N 21/3563* | (2014.01) |
| *G01N 21/59* | (2006.01) |
| *G01N 21/95* | (2006.01) |
| *G01N 21/88* | (2006.01) |
| *H01L 21/322* | (2006.01) |
| *H01S 3/02* | (2006.01) |
| *H01S 3/094* | (2006.01) |
| *H01S 3/109* | (2006.01) |
| *H01S 3/16* | (2006.01) |
| *G01N 21/35* | (2014.01) |
| *G01N 21/84* | (2006.01) |

(52) U.S. Cl.
CPC ......... *C30B 33/02* (2013.01); *G01N 21/3563* (2013.01); *G01N 21/59* (2013.01); *G01N 21/8806* (2013.01); *G01N 21/9501* (2013.01); *H01L 21/322* (2013.01); *H01S 3/027* (2013.01); *H01S 3/094* (2013.01); *H01S 3/109* (2013.01); *H01S 3/1666* (2013.01); *G01N 2021/3568* (2013.01); *G01N 2021/3595* (2013.01); *G01N 2021/8477* (2013.01); *G01N 2021/8822* (2013.01); *G01N 2201/06113* (2013.01)

(58) Field of Classification Search
USPC ...................................................... 356/239.1
See application file for complete search history.

(56) References Cited

U.S. PATENT DOCUMENTS

| | | | |
|---|---|---|---|
| 5,108,176 A | 4/1992 | Malin et al. | |
| 5,189,481 A | 2/1993 | Jann et al. | |
| 5,377,001 A | 12/1994 | Malin et al. | |
| 5,377,002 A | 12/1994 | Malin et al. | |
| 5,563,702 A | 10/1996 | Emery et al. | |
| 5,712,701 A | 1/1998 | Clementi et al. | |
| 5,998,313 A | 12/1999 | Sasaki et al. | |
| 5,999,310 A | 12/1999 | Shafer et al. | |
| 6,118,525 A | 9/2000 | Fossey et al. | |
| 6,201,601 B1 | 3/2001 | Vaez-Iravani et al. | |
| 6,249,371 B1 | 6/2001 | Masuda et al. | |
| 6,255,197 B1 | 7/2001 | Fujimura et al. | |
| 6,271,916 B1 | 8/2001 | Marxer et al. | |
| 6,358,784 B1 * | 3/2002 | Zhang .................. | B60R 25/066 257/E21.141 |
| 6,391,810 B1 | 5/2002 | Lenhart | |
| 6,440,864 B1 | 8/2002 | Kropewnicki et al. | |
| 6,489,248 B2 | 12/2002 | Zhang et al. | |
| 6,497,999 B1 | 12/2002 | Bryant et al. | |
| 6,576,411 B1 | 6/2003 | Irving et al. | |
| 6,590,698 B1 | 7/2003 | Ohtsuki et al. | |
| 6,608,676 B1 | 8/2003 | Zhao et al. | |
| 6,667,828 B2 * | 12/2003 | Shull .................. | H01S 3/109 359/330 |
| 6,816,520 B1 | 11/2004 | Tulloch et al. | |
| 7,037,813 B2 | 5/2006 | Collins et al. | |
| 7,088,443 B2 | 8/2006 | Vaez-Iravani et al. | |
| 7,136,402 B1 | 11/2006 | Ohtsuki | |
| 7,137,354 B2 | 11/2006 | Collins et al. | |
| 7,294,563 B2 | 11/2007 | Al-Bayati et al. | |
| 7,339,961 B2 | 3/2008 | Tokuhisa et al. | |
| 7,352,457 B2 | 4/2008 | Kvamme et al. | |
| 7,471,705 B2 | 12/2008 | Gerstenberger et al. | |
| 7,492,451 B2 | 2/2009 | Vaez-Iravani et al. | |
| 7,525,649 B1 | 4/2009 | Leong et al. | |
| 7,593,437 B2 | 9/2009 | Staroudoumov et al. | |
| 7,593,440 B2 | 9/2009 | Spinelli et al. | |
| 7,623,557 B2 | 11/2009 | Tokuhisa et al. | |
| 7,629,236 B2 * | 12/2009 | Wang .................... | H01L 31/072 136/249 |
| 7,643,529 B2 | 1/2010 | Brown et al. | |
| 7,715,459 B2 | 5/2010 | Brown et al. | |
| 7,920,616 B2 | 4/2011 | Brown et al. | |
| 7,948,673 B2 | 5/2011 | Yoshimura et al. | |
| 7,957,066 B2 | 6/2011 | Armstrong et al. | |
| 8,298,335 B2 | 10/2012 | Armstrong | |
| 8,518,283 B2 | 8/2013 | Yamamoto et al. | |
| 8,873,596 B2 | 10/2014 | Dribinski et al. | |
| 8,916,768 B2 * | 12/2014 | Ulyashin ........... | H01L 31/02167 136/256 |
| 9,459,215 B2 * | 10/2016 | Chuang .................. | C30B 29/10 |
| 9,605,998 B2 * | 3/2017 | Nozawa ................ | G01J 1/0407 |
| 2001/0023136 A1 | 9/2001 | Yang et al. | |
| 2002/0109110 A1 | 8/2002 | Some et al. | |
| 2003/0011872 A1 * | 1/2003 | Shull ....................... | H01S 3/109 359/333 |
| 2003/0148565 A1 * | 8/2003 | Yamanaka .......... | H01L 21/2026 438/200 |
| 2005/0136604 A1 | 6/2005 | Al-Bayati et al. | |
| 2006/0035450 A1 * | 2/2006 | Frank ................ | H01L 21/76254 438/585 |
| 2006/0199396 A1 | 9/2006 | Tsai et al. | |
| 2007/0002465 A1 | 1/2007 | Chuang et al. | |
| 2007/0137823 A1 | 6/2007 | Haran | |
| 2007/0212811 A1 | 9/2007 | Hanawa et al. | |
| 2009/0180176 A1 | 7/2009 | Armstrong et al. | |
| 2009/0185583 A1 | 7/2009 | Kuksenkov et al. | |
| 2009/0221149 A1 | 9/2009 | Hammond, IV et al. | |
| 2009/0277872 A1 | 11/2009 | Yamamoto et al. | |
| 2009/0296755 A1 | 12/2009 | Brown et al. | |
| 2011/0073982 A1 | 3/2011 | Armstrong et al. | |
| 2011/0079884 A1 | 4/2011 | Basim | |
| 2011/0134944 A1 | 6/2011 | Kaneda et al. | |
| 2011/0164648 A1 | 7/2011 | Dribinski | |
| 2011/0228263 A1 | 9/2011 | Chuang et al. | |
| 2011/0279819 A1 | 11/2011 | Chuang et al. | |
| 2012/0160856 A1 | 6/2012 | Armstrong | |
| 2012/0314286 A1 | 12/2012 | Chuang et al. | |
| 2013/0077086 A1 | 3/2013 | Chuang et al. | |
| 2014/0111799 A1 | 4/2014 | Lei et al. | |
| 2015/0053908 A1 * | 2/2015 | Fowler .................... | H01L 45/04 257/4 |
| 2016/0061655 A1 * | 3/2016 | Nozawa ................ | G01S 17/10 250/578.1 |

FOREIGN PATENT DOCUMENTS

| | | |
|---|---|---|
| JP | H0511287 A | 1/1993 |
| JP | H09328395 A | 12/1997 |
| JP | 200166654 A | 9/2002 |
| JP | 2004233163 A | 8/2004 |
| JP | 2009-145791 A | 7/2009 |
| JP | 2010-054547 A | 3/2010 |
| JP | 2010-256784 A | 10/2010 |
| JP | 2011158869 A | 8/2011 |
| WO | 2009014894 A1 | 1/2009 |
| WO | 2010/037106 A2 | 4/2010 |
| WO | 2013052878 A1 | 4/2013 |

OTHER PUBLICATIONS

A. Shirakawa et al., High-power Yb-doped photonic bandgap fiber amplifier at 1150-1200 nm, Optics Express, Jan. 19, 2009, vol. 17, No. 2, p. 447-454.

Masahiro Kashiwagi et al., Over 10 W Output Linearly-Polarized Single-Stage Fiber Laser Oscillating Above 1160 nm Using Yb-Doped Polarization-Maintaining Solid Photonic Bandgap Fiber,

(56) References Cited

OTHER PUBLICATIONS

IEEE Journal of Quantum Electronics, vol. 47, No. 8, Aug. 2011, pp. 1136-1141.
Mridu P. Kalita et al., Multi-watts narrow-linewidth all fiber Yb-doped laser operating at 1179 nm, Optics Express, Mar. 15, 2010, vol. 18. No. 6, p. 5920-5925.
E.M. Dianov et al., Bi-doped Fiber Lasers: New Type of High-Power Radiation Sources, © 2006 Optical Society of America, 2 pages.
S. Yoo et al., Excited state absorption measurement in bismuth-doped silicate fibers for use in 1160 nm fiber laser, Optoelectronics Research Centre, 1 page.
Valerii V. Ter-Mikirtychev et al., Tunable LiF:FT Color Center Laser with an Intracavity Integrated-Optic Output Coupler, Journal of Lightwave Technology, vol. 14, No. 10, Oct. 1996, p. 2353-2355.
Jun Sakuma et al., True CW 193.4-nm light generation based on frequency conversion of fiber amplifiers, © 2011 Optical Society of America, Aug. 1, 2011, vol. 19, No. 16, Optics Express, p. 15020-15025.
Office Action dated Sep. 19, 2018 for EP Application No. 12838919.4.
Office Action dated Mar. 5, 2019 for JP Patent Application No. 2018-074155.

\* cited by examiner

PASSIVATION OF NONLINEAR OPTICAL CRYSTALS

CROSS-REFERENCE TO RELATED APPLICATION

The present application is related to and claims the benefit of the earliest available effective filing date(s) from the following listed application(s) (the "Related Applications") (e.g., claims earliest available priority dates for other than provisional patent applications or claims benefits under 35 USC § 119(e) for provisional patent applications, for any and all parent, grandparent, great-grandparent, etc. applications of the Related Application(s)).

RELATED APPLICATIONS

The present application constitutes a continuation patent application of United States Non-Provisional Patent Application entitled PASSIVATION OF NONLINEAR OPTICAL CRYSTALS, naming Yung-Ho Chuang and Vladimir Dribinski as inventors, filed Jan. 29, 2016, U.S. application Ser. No. 15/010,331, which in turn constitutes a continuation patent application of United States Non-Provisional Patent Application entitled PASSIVATION OF NONLINEAR OPTICAL CRYSTALS, naming Yung-Ho Chuang and Vladimir Dribinski as inventors, filed Jun. 5, 2012, U.S. application Ser. No. 13/488,635, which in turn constitutes a regular (non-provisional) patent application of United States Provisional Patent Application entitled NLO CRYSTAL PROPERTIES BY HYDROGEN PASSIVATION, naming Yung-Ho Chuang and Vladimir Dribinski as inventor, filed Oct. 7, 2011, Application Ser. No. 61/544,425. Each of the above applications is incorporated herein by reference in their entirety.

TECHNICAL FIELD

The present invention relates to the field of nonlinear optical materials, and in particular to a system and method for passivating nonlinear optical crystals to cure crystal defects.

BACKGROUND

Many modern-day laser systems require nonlinear optical (NLO) elements. For example, NLO elements are commonly used in applications such as frequency mixing (e.g. harmonic generation, parametric generation/amplification, and the like), Raman amplification, Kerr-lens mode-locking, electro-optic modulation, acousto-optic modulation, and others.

Laser-induced damage (LID) of NLO elements is a major limitation of many modern laser systems. LID occurs as a result of the interaction between laser radiation and the material making up a given NLO element. Accordingly, over time, NLO elements incur LID, which may negatively impact such physical properties as transmittance, reflectivity, refraction indices, and the like. In turn, this degradation of physical properties due to accrued LID eventually leads to failure of NLO elements within a laser system.

LID becomes even more problematic in laser systems that utilize shorter wavelengths of the electromagnetic spectrum, such as deep ultraviolet (DUV) light, with wavelengths less than 300 nm. In addition, laser-induced damage rates are also impacted by material defects present in NLO elements, such as dislocations, impurities, vacancies, and the like. In most cases, material defects in a given NLO element leads to the NLO element being less resistant to LID. Accordingly, the NLO elements have a shorter lifetime as a result of material defects.

The present invention is directed to mitigating the foregoing problems by improving damage resistance of NLO elements utilizing a novel system and method disclosed herein.

SUMMARY

A laser system is disclosed, in accordance with one or more embodiments of the present disclosure. In one embodiment, the laser system includes a nonlinear optical (NLO) crystal. In another embodiment, the NLO crystal is annealed within a selected temperature range. In another embodiment, the NLO crystal is passivated with at least one of hydrogen, deuterium, a hydrogen-containing compound or a deuterium-containing compound to a selected passivation level. In another embodiment, the laser system includes at least one light source. In another embodiment, the laser system is configured to generate light of a selected wavelength. In another embodiment, the light source is further configured to transmit light through the NLO crystal. In another embodiment, the laser system includes a crystal housing unit configured to house the NLO crystal.

A nonlinear optical (NLO) crystal is disclosed, in accordance with one or more embodiments of the present disclosure. In one embodiment, the NLO crystal is annealed within a selected temperature range. In another embodiment, the NLO crystal is passivated with at least one of hydrogen, deuterium, a hydrogen-containing compound or a deuterium-containing compound to a selected passivation level.

A method for passivating crystal defects of a nonlinear (NLO) crystal is disclosed, in accordance with one or more embodiments of the present disclosure. In one embodiment, the method includes providing a nonlinear optical (NLO) crystal. In another embodiment, the method includes maintaining a temperature of the NLO crystal within a selected temperature range below a melting temperature of the NLO crystal. In another embodiment, the method includes exposing the NLO crystal to passivating gas having a concentration of at least one of hydrogen, deuterium, a hydrogen-containing compound and a deuterium-containing compound at or near a selected concentration to repair at least one of dangling bonds or broken bonds within the NLO crystal.

A method for passivating crystal defects of a nonlinear (NLO) crystal is disclosed, in accordance with one or more embodiments of the present disclosure. In one embodiment, the method includes providing an NLO crystal. In another embodiment, the method includes performing an annealing process on the NLO crystal to reduce water or OH content of the NLO crystal. In another embodiment, the method includes exposing the NLO crystal to passivating gas having a concentration of at least one of hydrogen, deuterium, a hydrogen-containing compound and a deuterium-containing compound at or near a selected concentration to repair at least one of dangling bonds or broken bonds within the NLO crystal.

It is to be understood that both the foregoing general description and the following detailed description are exemplary and explanatory only and are not necessarily restrictive of the invention as claimed. The accompanying drawings, which are incorporated in and constitute a part of the specification, illustrate embodiments of the invention and together with the general description, serve to explain the principles of the invention.

BRIEF DESCRIPTION OF THE DRAWINGS

The numerous advantages of the disclosure may be better understood by those skilled in the art by reference to the accompanying figures in which.

DETAILED DESCRIPTION OF THE INVENTION

Reference will now be made in detail to the subject matter disclosed, which is illustrated in the accompanying drawings.

Referring generally to FIGS. 1A through 5, a system and method for passivating a nonlinear optical (NLO) crystal is described in accordance with the present disclosure. Laser systems commonly utilize NLO crystals for many applications such as frequency mixing, Raman amplification, Kerr-lens mode-locking, electro-optic modulation, and acousto-optic modulation, among others. Exposure to electromagnetic radiation within a laser system affects physical properties (e.g., transmittance, reflectivity, refraction indices, etc.) of NLO crystals. The resulting changes to the physical properties of NLO crystals are commonly referred to as laser-induced damage (LID) and tend to impair NLO crystals from functioning properly. NLO crystals are less resistant to LID when they have a greater quantity or amount of crystal defects such as dislocations, impurities, vacancies, and the like. The present invention is directed to a system and method for curing crystal defects of an NLO crystal utilizing hydrogen passivation and/or crystal annealing.

As used throughout the present disclosure, the term "crystal", "NLO crystal", or "nonlinear crystal" generally refers to a nonlinear optical crystal suitable for frequency conversion. For example, the nonlinear optical crystal of the present invention may be configured to frequency convert incident illumination of a first wavelength (e.g., 532 nm) to an output illumination of a shorter wavelength (e.g., 266 nm). Further, the nonlinear optical crystal of the present invention may include, but is not limited to, beta-Barium Borate (BBO), Lithium Triborate (LBO), Lithium Tetraborate (LTB), Cesium Lithium Borate (CLBO), Cesium Borate (CBO), oxide-type non-linear crystals, and the like.

As used throughout the present disclosure, the term "wafer" generally refers to a substrate formed of a semiconductor or non-semiconductor material. For example, semiconductor or non-semiconductor materials include, but are not limited to, monocrystalline silicon, gallium arsenide, and indium phosphide. A wafer may include one or more layers. For example, such layers may include, but are not limited to, a resist, a dielectric material, a conductive material, and a semiconductive material. Many different types of such layers are known in the art, and the term wafer as used herein is intended to encompass a wafer on which all types of such layers may be formed.

Figure 1A:
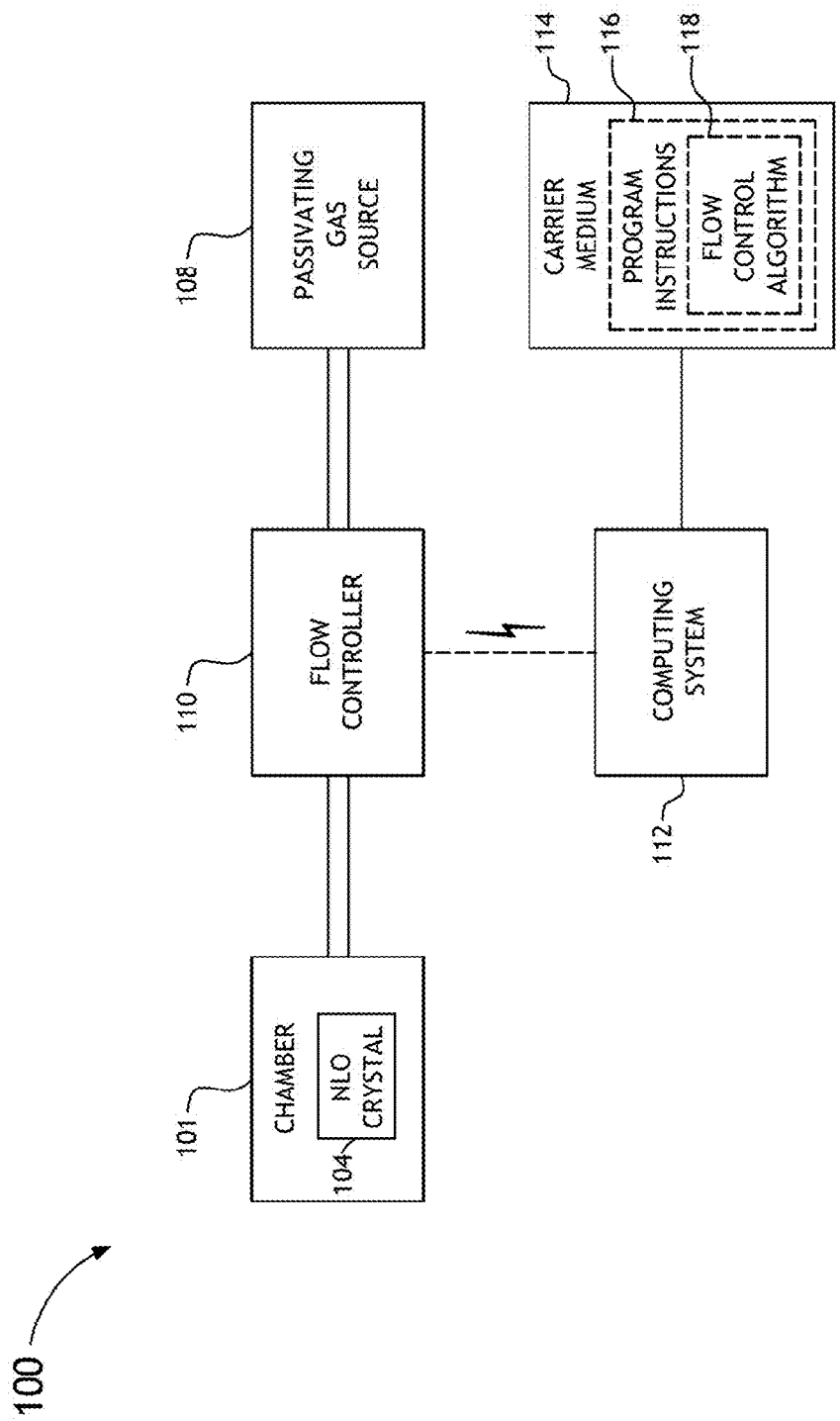
FIG. 1A is a block diagram illustrating a system for passivating a NLO crystal, in accordance with one embodiment of the present invention.
Figure 1B:
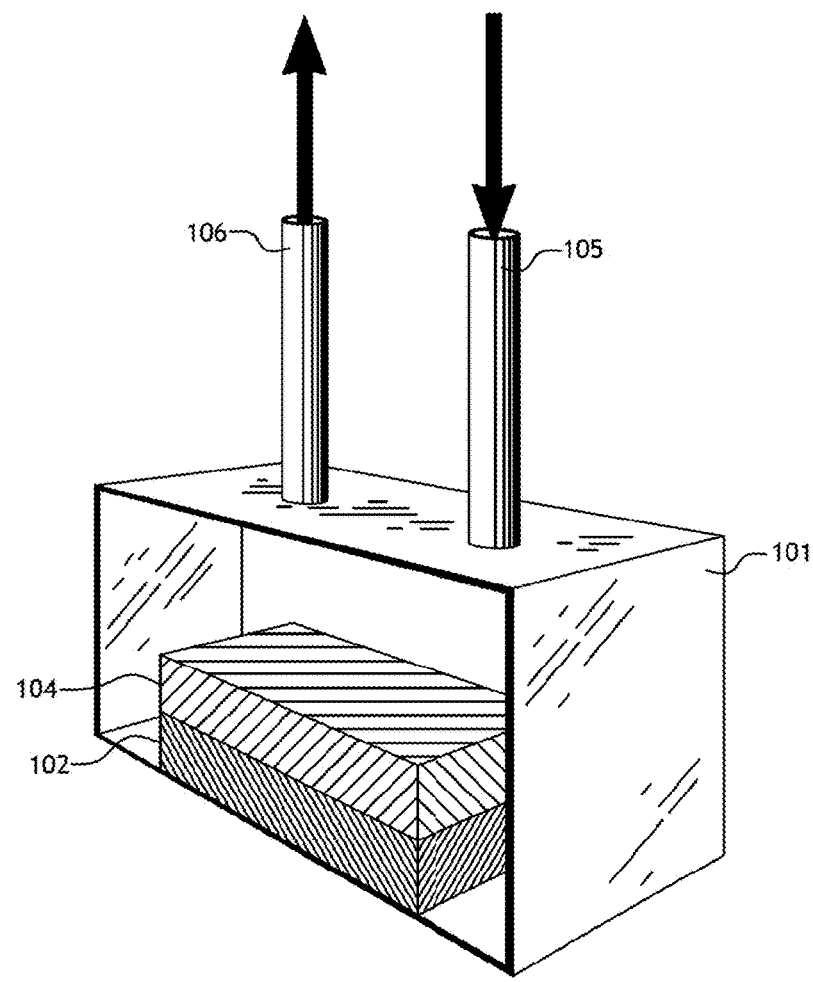
FIG. 1B illustrates a conceptual view of an exposure chamber of a system for passivating a NLO crystal, in accordance with one embodiment of the present invention.

FIGS. 1A and 1B illustrate a system 100 for passivating a NLO crystal 104 in order to cure crystal defects within the crystal. These defects may be cured through the attachment of hydrogen atoms to dangling or broken bonds within the crystal 104. For example, the dangling or broken bonds may include dangling oxygen bonds, which are often a primary type of defect that affects physical/optical properties as well as NLO crystal lifetime. In one embodiment, the system 100 may include an exposure chamber 101 configured to contain a volume of passivating gas. The exposure chamber 101 may be further configured to contain the NLO crystal 104 such that the NLO crystal 104 may be exposed to the passivating gas contained within the exposure chamber 101. In addition, the exposure chamber 101 may be further configured to contain a substrate 102 configured to hold the NLO crystal 104 while the NLO crystal 104 is exposed to passivating gas contained within the exposure chamber 101. Alternatively, the substrate 102 may be a portion of an interior surface of the chamber 101.

The passivating gas of the present invention may include a gaseous mixture of two or more gases having a selected concentration of hydrogen. In one embodiment, the gas mixture may include molecular hydrogen ($H_2$). In another embodiment, the passivating gas may include a low-molecular-weight gas that may yield hydrogen upon chemical reaction or dissociation. Such low-molecular-weight gases may include, but are not limited to, $NH_3$ or $CH_4$. The desired concentration of hydrogen may include a concentration exceeding the natural abundance of hydrogen present under normal atmospheric conditions. In this regard, the hydrogen concentration of the passivating gas may consist of a concentration in excess of the hydrogen concentration naturally present in air. In another aspect, the desired concentration of hydrogen may also be a user selected concentration or a concentration determined utilizing one or more physical attributes of the NLO crystal 104. The passivating gas mixture may further include an inert gas such as argon, nitrogen, helium or the like.

In a further embodiment, the passivating gas of the present invention may include a gas mixture having a hydrogen concentration in the range of 5 to 10%. It is noted herein that this hydrogen concentration range is not a limitation and is presented merely for purposes of illustration. It is contemplated that the hydrogen concentration level of the passivating gas may include any range suitable for the given application. In a further embodiment, the hydrogen concentration of the passivating gas mixture may include a heavy isotope of hydrogen, deuterium, for improved passivation results. The exact amount of deuterium in the mixture may be determined by optimizing passivation results and may vary from a fraction of total hydrogen concentration to 100% of all the hydrogen in the mixture.

In an embodiment, the system may further include a passivating gas source 108 fluidically coupled to the exposure chamber 101 and configured to supply the exposure chamber with passivating gas. The exposure chamber 101 may include a gas inflow port 105 configured to receive passivating gas from the passivating gas source 108 and further configured to transmit passivating gas received from the passivating gas source 108 to an interior portion of the exposure chamber 101. The exposure chamber 101 may further include a gas outflow port 106 configured to release passivating gas from the interior portion of the exposure chamber 101.

In a further embodiment, the system 100 may include a flow controller 110 fluidically connected in between the passivating gas source 108 and the exposure chamber 101. The flow controller 110 may be configured to control the rate at which passivating gas is supplied to the exposure chamber 101. The flow controller 110 may include a valve, regulator, or any other means for regulating the pressure or rate at which passivating gas moves through at least one conduit fluidically connecting the flow controller 110 to the exposure chamber 101. The flow controller may be further configured to be fluidically connected to the gas inflow port 105 of the exposure chamber and further configured to control the rate at which passivating gas is supplied through the gas inflow port 105 to the interior portion of the exposure chamber 101. In another embodiment, the flow controller 110 or an additional flow controller (not shown) may be configured to be fluidically connected to the gas outflow port 106 of the exposure chamber 101 and further configured to control the rate at which passivating gas is removed from the interior portion of the exposure chamber 101.

In another embodiment, the system 100 may further include one or more computing systems 112 communicatively coupled to the flow controller 110. The computing system 112 may be configured to provide the flow controller 110 with instructions for controlling the rate at which passivating gas is supplied to the exposure chamber 101. The computing system 112 may be further configured to provide the flow controller 110 or an additional flow controller (not shown) with instructions for controlling the rate at which passivating gas is removed from the exposure chamber 101. The computing system may contain a carrier medium 114 such as a flash, solid-state, optical, random access or other static or dynamic memory device configured with program instructions 116 including a flow control algorithm 118. Flow control algorithms 118 are known to the art, such as algorithms for configuring a pressure valve that may be included in the flow controller 110. For example, the flow control algorithm 118 may direct the flow controller 110 to actuate the pressure valve based on a correlation between the pressure valve's mechanical properties and a desired flow rate. In some embodiments, a user selected flow rate of 10 to 200 $cm^3$/min may be a desirable flow rate for passivating the NLO crystal 104 contained within the exposure chamber 101. However, flow rates outside of the 10 to 200 $cm^3$/min range may be desirable depending on the passivating gas mixture or the composition of the NLO crystal 104. The foregoing flow rate range is exemplary only and is not intended to limit the present invention in any way.

In a further embodiment, the substrate 102 configured to hold the NLO crystal 104 within the exposure chamber 101 may be further configured to control the temperature of the NLO crystal 104. In one aspect, a user may select a temperature greater than ambient or room temperature, but less than the melting temperature of the NLO crystal 104. For example, the substrate 102 may be configured to heat the NLO crystal 104 to a range of 300 to 350° C. or some other selected temperature to improve hydrogen penetration into the crystal, alleviate decomposition of molecular hydrogen (e.g., $H_2$) or other hydrogen-containing molecule into atomic hydrogen, or eliminate undesirable reaction products between hydrogen and the NLO crystal 104 (e.g. weak OH bonds, water, or the like). It is contemplated herein that the substrate 102 may be configured to increase, decrease, and/or maintain the temperature of the NLO crystal 104 at any feasible temperature or range of temperatures desirable for successfully passivating the NLO crystal 104. Accordingly, the foregoing temperature range is exemplary only and is not intended to limit the present invention in any way.

Figure 2A:
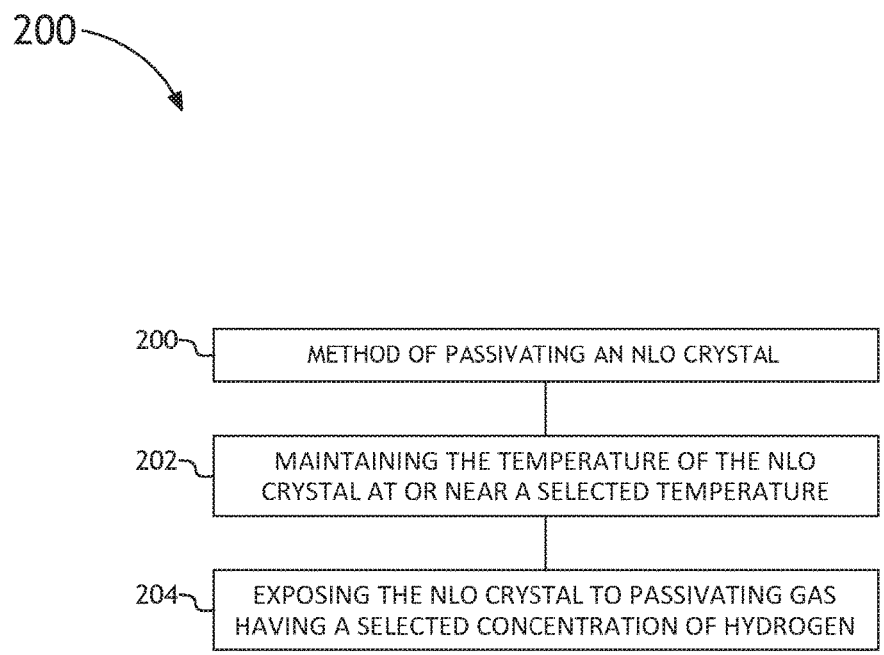
FIG. 2A is a flow diagram illustrating a method for passivating a NLO crystal, in accordance with one embodiment of the present invention.

In accordance with the foregoing system 100, FIGS. 2A through 2D illustrate flow diagrams for a method 200 for passivating the NLO crystal 104 with hydrogen in order to cure crystal defects caused by dangling or broken bonds. Referring to FIG. 2A, the method 200 may include one or more of the following steps: (i) step 202, maintaining the temperature of the NLO crystal 104 at or near a selected temperature that is a user selected temperature or a temperature determined utilizing one or more attributes of the NLO crystal 104 (e.g., composition, water content, defect level, etc.); and (ii) step 204, exposing the NLO crystal 104 to passivating gas having a selected concentration of hydrogen that is a user selected hydrogen concentration or a hydrogen concentration determined utilizing one or more attributes of the NLO crystal 104.

In step 202, the temperature of the NLO crystal 104 may be controlled by any heating and/or cooling element (hereinafter "heating element") such as the substrate 102 configured to hold the NLO crystal 104 in the exposure chamber 101 of the system 100. The heating element may be configured to heat or cool the NLO crystal 104 to the selected temperature which may be a user selected temperature, a temperature determined utilizing one or more attributes of the NLO crystal 104, or any temperature that improves hydrogen penetration into the crystal, alleviates decomposition of $H_2$ molecules into H atoms, or eliminates undesirable products from one or more reactions between hydrogen and the NLO crystal 104 (e.g. weak OH bonds, water, etc.). For example, in one embodiment the selected temperature may be a temperature in the range of approximately 300 to 350° C. The heating element may be further configured to maintain the temperature of the NLO crystal 104 at or near the selected temperature for a selected period of time such as the time required to adequately passivate the NLO crystal 104. For example, the time required to adequately passivate the NLO crystal 104 may be in the range of approximately 100 to 200 hours. Accordingly, in one embodiment, the heating element may be configured to maintain the temperature of the NLO crystal 104 at or near the selected temperature for the selected period of time in the range of approximately 100 to 200 hours. The foregoing temperatures and time durations are included by way of example only, and it is contemplated that these parameters may be significantly altered without departing from the essence of this disclosure. Accordingly, nothing herein should be construed to limit the present invention in any way.

In step 204, the NLO crystal 104 may be exposed to passivating gas within an atmospherically controlled container such as the exposure chamber 101 of the system 100. The passivating gas may be a gas mixture having a selected concentration of hydrogen. The selected hydrogen concentration may be a user selected concentration, a concentration determined utilizing one or more attributes of the NLO crystal 104, or any acceptable concentration for curing crystal defects of the NLO crystal 104 by attaching hydrogen atoms from the passivating gas to broken or dangling bonds of the NLO crystal 104. For example, in one embodiment, the selected hydrogen concentration of the passivating gas may be a hydrogen concentration in the range of approximately 5 to 10% of the passivating gas mixture. However, the foregoing hydrogen concentration is only included by way of example, and it is not intended to limit the present invention in any way.

Figure 2B:
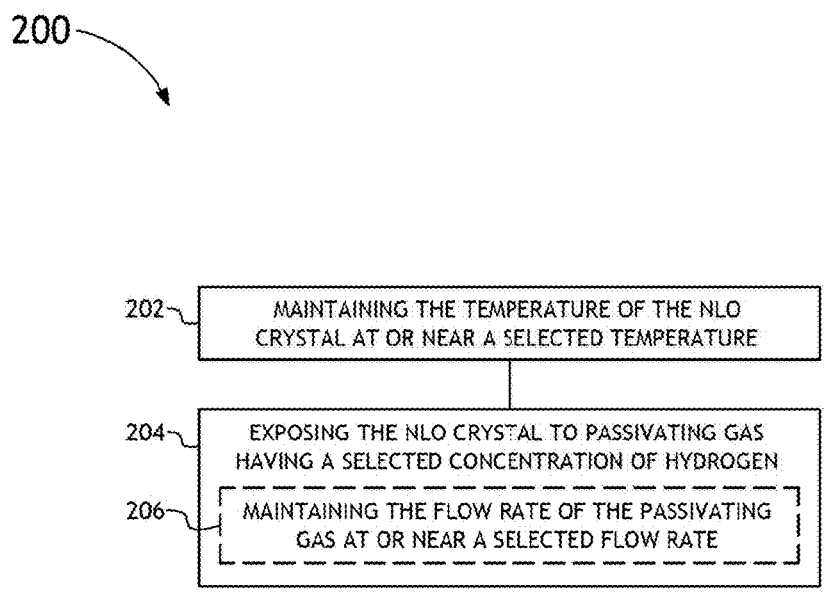
FIG. 2B is a flow diagram illustrating a method for passivating a NLO crystal, in accordance with one embodiment of the present invention.

Referring to FIG. 2B, step 204 may include a step 206 of maintaining the flow rate at which the passivating gas may flow through the container at or near a selected flow rate such as a user selected flow rate, a flow rate determined utilizing one or more attributes of the NLO crystal 104, a flow rate acceptable for maintaining the hydrogen concentration of passivating gas within the container at or near the selected hydrogen concentration, or any flow rate sufficient for curing crystal defects of the NLO crystal 104 by attaching hydrogen atoms from the passivating gas to broken or dangling bonds of the NLO crystal 104. The flow rate may be regulated by the flow controller 110 of the system 100 or by any valve, regulator, or other means for controlling the pressure or rate at which gas moves through one or more conduits. For example, in one embodiment, the flow controller 110 may be configured to regulate the flow rate of passivating gas flowing through the exposure chamber 101 to the selected flow rate in the range of approximately 10 to 200 cm$^3$/min. However, the foregoing range of flow rates is included by way of example only, and it should not be construed to limit the present invention in any way.

Figure 2C:
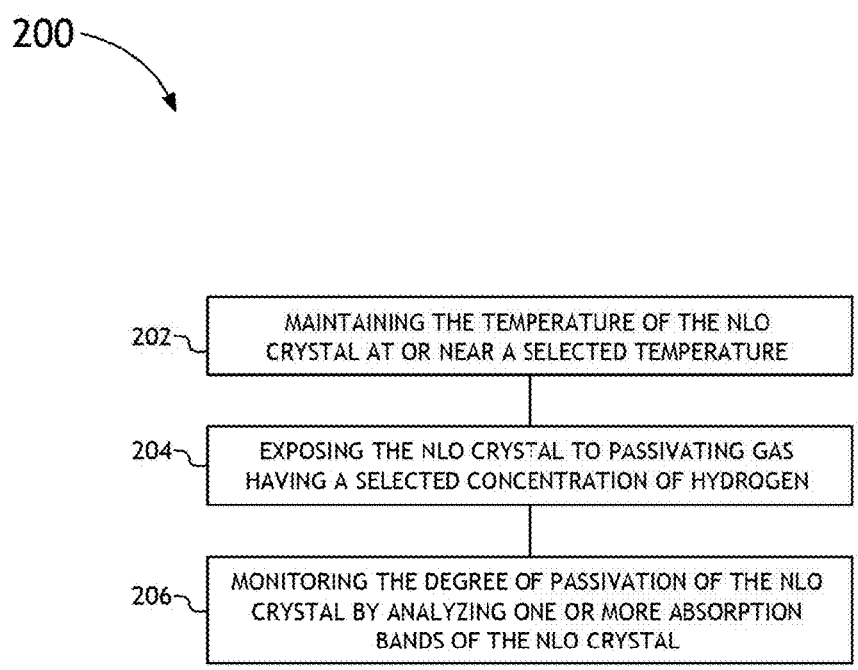
FIG. 2C is a flow diagram illustrating a method for passivating a NLO crystal, in accordance with one embodiment of the present invention.
Figure 2D:
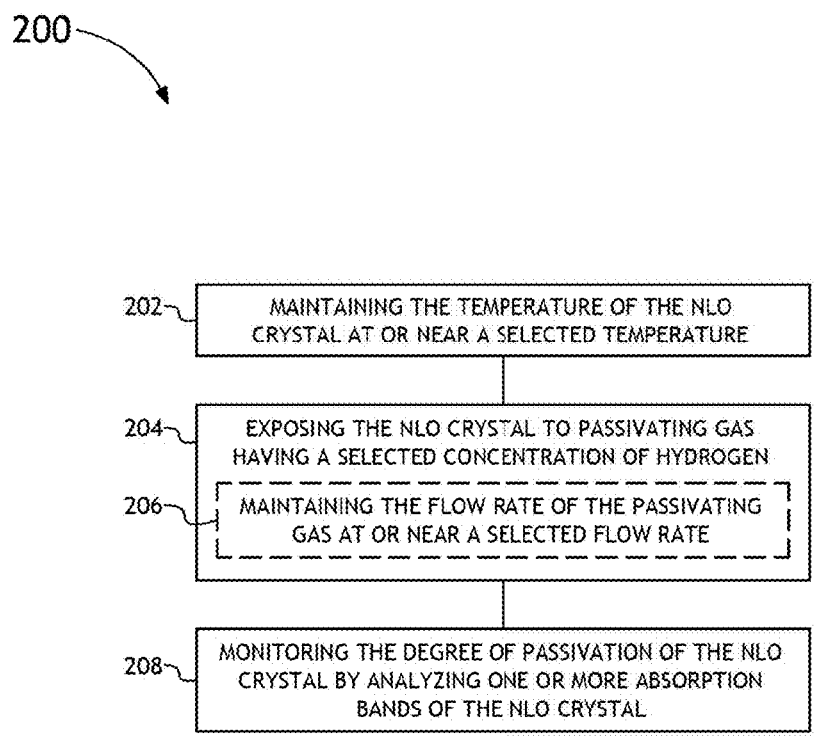
FIG. 2D is a flow diagram illustrating a method for passivating a NLO crystal, in accordance with one embodiment of the present invention.

Referring to FIGS. 2C and 2D, one embodiment of the method 200 may further include a step 208 of monitoring a degree of passivation of the NLO crystal 104. The degree of passivation may be correlated to an amount or change in amount of OH bonds of the NLO crystal 104 because the amount of OH bonds generally increases as the NLO crystal 104 is passivated as a result of having hydrogen atoms attach to dangling oxygen bonds of the NLO crystal 104. Accordingly, the degree of passivation may be monitored by analyzing one or more absorption bands of the NLO crystal 104, wherein the absorption band is affected by a change in the number of OH bonds of the NLO crystal 104. The absorption band may be analyzed by using any method known to the art for detecting a level at which the NLO crystal 104 absorbs illumination having one or more wavelengths. In one embodiment, the degree of passivation may be monitored utilizing Fourier Transform Infrared Spectroscopy (FTIR). For example, utilizing Fourier Transform Infrared Spectroscopy (FTIR), the degree of passivation of the NLO crystal 104 may be monitored through the observation of at least one absorption band in the Infrared (IR) spectrum of the NLO crystal 104. An FTIR process for monitoring the degree of passivation of the NLO crystal 104 may include one or more of the following steps: (i) transmitting illumination having one or more wavelengths through the NLO crystal 104; (ii) detecting illumination transmitted through the NLO crystal 104; (iii) determining an amount of illumination absorbed by the NLO crystal 104 at one or more wavelengths utilizing information about illumination transmitted through the NLO crystal 104; and (iv) determining the degree of passivation of the NLO crystal 104 utilizing a correlation between illumination absorbed by the NLO crystal 104 at one or more wavelengths and the amount or change in amount of OH bonds of the NLO crystal 104.

In a further embodiment of the method 200, the NLO crystal 104 may be exposed to passivating gas in step 204 until the NLO crystal 104 is sufficiently passivated. The step 208 of monitoring the degree of passivation of the NLO crystal 104 may be utilized to determine whether or not the NLO crystal 104 has been sufficiently passivated. For example, the degree of passivation of the NLO crystal 104 may be determined by observing one or more absorption bands of the NLO crystal 104 appearing or changing intensity at one or more wavelengths of the IR spectrum in the range of approximately 3200 to 4000 cm$^{-1}$, wherein the amplitude or intensity of the absorption band appearing or changing intensity at the wavelength correlates to the amount or change in amount of OH bonds of the NLO crystal 104. For instance, FTIR may be used to monitor the absorption of —OH bonds (including H$_2$O) near 3580 cm$^{-1}$ in the infra-red spectrum. For example, FTIR monitoring may be performed in-situ, wherein a crystal is monitored with FTIR while it is undergoing passivation. Step 208 may further determine whether or not the NLO crystal 104 has been sufficiently passivated by monitoring the relative change in the integrated peak intensity of one or more selected peaks in the FTIR absorption spectra. For instance, step 208 may determine sufficient passivation when a 5% reduction in an —OH absorption peak is observed.

The foregoing range of absorption band wavelengths and the percentage change for sufficient passivation are included by way of example only and it is contemplated that one or more absorption bands may appear at other wavelengths in the IR, visible, and/or UV spectra; accordingly, the foregoing range of wavelengths is not intended to limit the present invention in any way.

The foregoing steps are neither sequential nor mandatory and may occur in any order or concurrent with one another. For example, it is contemplated that in one embodiment of the method 200, the NLO crystal 104 may be exposed to passivating gas as provided for in step 204; and concurrently, the degree of passivation of the NLO crystal 104 may be monitored utilizing FTIR as provided for in step 208. In some instances it may be advantageous to combine some or all of the steps and to arrange the steps in a sequence that departs from the order in which the steps have been discussed herein. The discussion herein is explanatory only and is not intended to limit the method or methods disclosed herein to any particular sequence, order, or combination of steps.

Figure 3A:
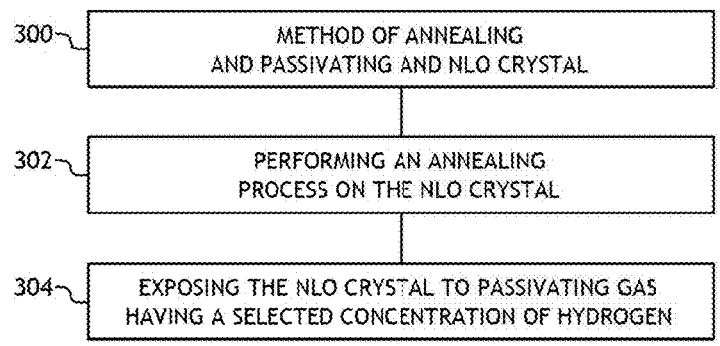
FIG. 3A is a flow diagram illustrating a method for annealing and passivating a NLO crystal, in accordance with one embodiment of the present invention.

FIGS. 3A through 3D illustrate a method 300 for passivating and annealing the NLO crystal 104. Referring to FIG. 3A, the method 300 may include one or more of the following steps: (i) step 302, performing an annealing process on the NLO crystal 104 to reduce the water or OH content of the NLO crystal 104; and (ii) step 304, exposing the NLO crystal 104 to passivating gas having a selected concentration of hydrogen that is a user selected hydrogen concentration or a hydrogen concentration determined utilizing one or more attributes of the NLO crystal 104.

In step 302, the NLO crystal 104 may undergo an annealing process in a dry atmosphere (e.g. clean dry air or dry inert gas) to remove at least a portion of water or OH molecules from the NLO crystal 104. Annealing processes are known to the art and may include one or more of the following steps: (i) increasing or decreasing the temperature of the NLO crystal 104 to a selected temperature such as a sufficiently high value for removing water molecules from the NLO crystal 104 without melting or damaging the NLO crystal 104; (ii) maintaining the temperature of the NLO crystal 104 at or near the selected temperature for a selected period of time such as a sufficient period of time to decrease water content of the NLO crystal 104 to a selected level; and (iii) increasing or decreasing the temperature of the NLO crystal 104 to a selected final temperature such as ambient or room temperature when water content of the NLO crystal 104 has been reduced to the selected level. The selected level of water content may be a user selected level, a water content level determined utilizing one or more attributes of the NLO crystal 104, or any water content level correlating to desired optical/physical performance or increased crystal lifetime.

In one embodiment, the annealing process of step 302 may further include a step of increasing or decreasing the temperature of the NLO crystal 104 to the selected temperature over a selected time interval. For example, the NLO crystal 104 may be heated to the selected temperature of approximately 150° C. gradually over the course of the selected time period of approximately 2 hours. The temperature of the NLO crystal 104 may be increased, decreased, or maintained by any known heating or cooling device. For instance, the substrate 102 may be equipped with a heating or cooling device suitable for heating or cooling the NLO crystal 104. In another instance, the chamber 101 may be configured as an oven or a refrigerator. The heating or cooling device may be further configured to maintain the temperature of the NLO crystal 104 at or near the selected temperature for a selected period of time such as a user selected time period or a time period determined utilizing one or more attributes of the NLO crystal 104. For example, the temperature of the NLO crystal 104 may be maintained at or near 150° C. for approximately 10 hours. Alternatively, the temperature of the NLO crystal 104 may be maintained at or near the selected temperature until the water or OH content of the NLO crystal 104 is sufficiently reduced. The foregoing temperatures, time periods, and time intervals are included by way of example only, and it is contemplated that these parameters may be significantly altered without departing from the essence of this disclosure. Accordingly, nothing herein should be construed to limit the present invention in any way.

In a further embodiment, the annealing process of step 302 may be repeated to further reduce the water content of the NLO crystal 104. The annealing process may be repeated utilizing the same or different parameters if necessary, such as one or more different temperatures or different time periods or intervals. For example, the NLO crystal 104 may be heated to approximately 200° C. over the course of approximately 1 hour. Similarly, the temperature of the NLO crystal 104 may be maintained at or near 200° C. for approximately 100 hours or until the water or OH content of the NLO crystal 104 is sufficiently reduced. The foregoing temperatures, time periods, and time intervals are included by way of example only, and it is contemplated that these parameters may be significantly altered without departing from the essence of this disclosure. Accordingly, nothing herein should be construed to limit the present invention in any way.

The annealing process of step 302 may further include the step of gradually increasing or decreasing the temperature of the NLO crystal 104 to the selected final temperature (e.g. ambient or room temperature) over a selected time interval. For example, the NLO crystal 104 may be gradually cooled or allowed to cool to ambient or room temperature over the course of approximately 3 hours or any other acceptable time interval. In one embodiment, the NLO crystal 104 may be cooled by having heat gradually removed so that the temperature of the NLO crystal 104 gradually decreases to ambient temperature over the selected time interval. In another embodiment, the NLO crystal 104 may be cooled utilizing a cooling device to decrease the temperature of the NLO crystal 104 to the selected final temperature. The selected time interval may be any user selected time interval or a time interval determined utilizing one or more attributes of the NLO crystal 104. Accordingly, any time interval included herein is included by way of example only and is not intended to limit the present invention in any way.

Figure 3B:
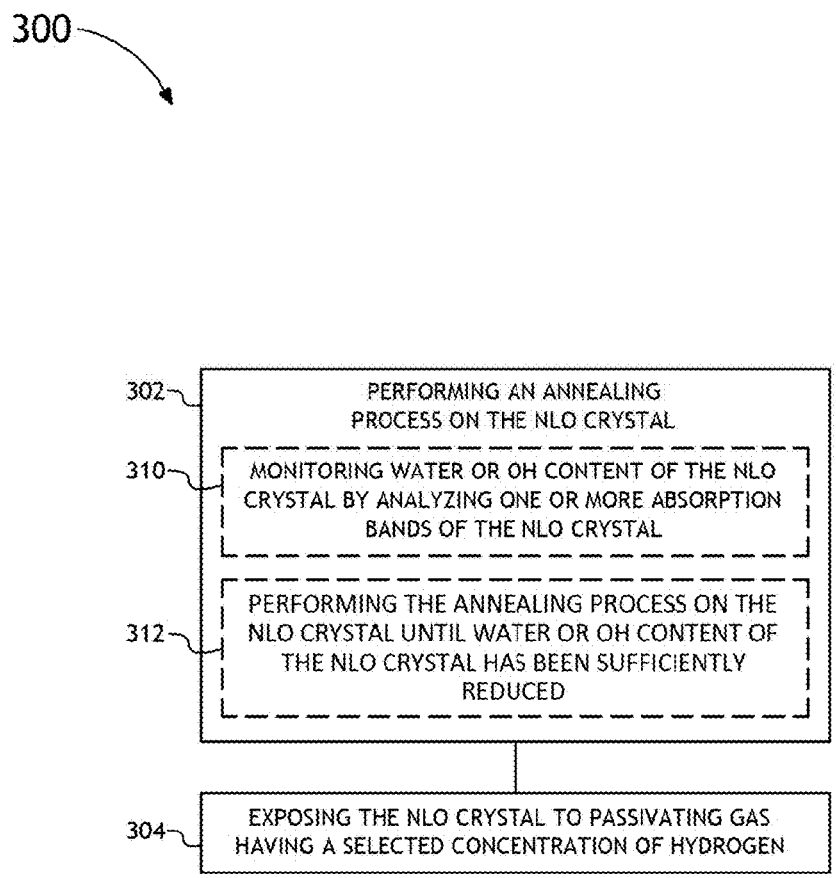
FIG. 3B is a flow diagram illustrating a method for annealing and passivating a NLO crystal, in accordance with one embodiment of the present invention.
Figure 3C:
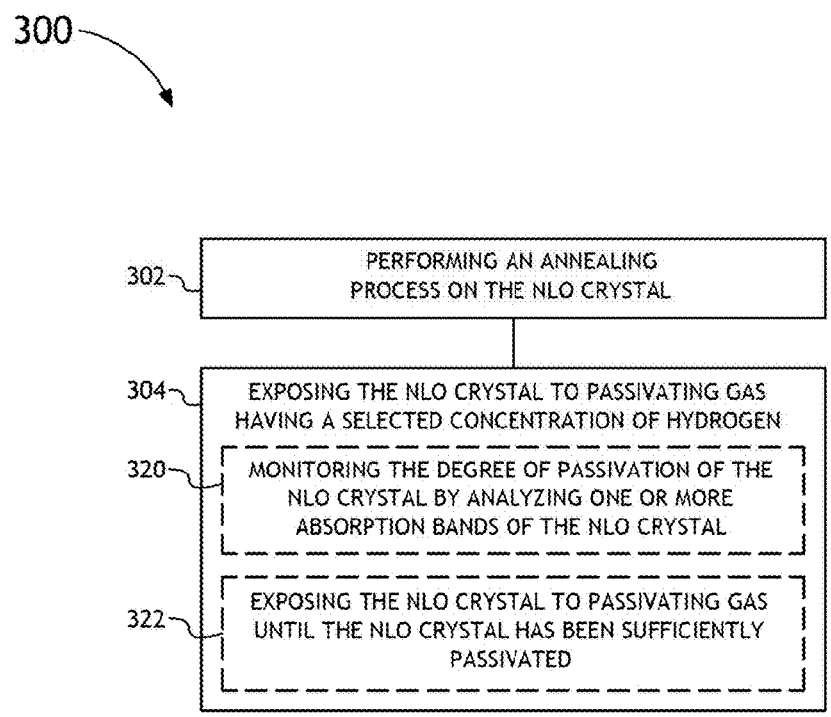
FIG. 3C is a flow diagram illustrating a method for annealing and passivating a NLO crystal, in accordance with one embodiment of the present invention.
Figure 3D:
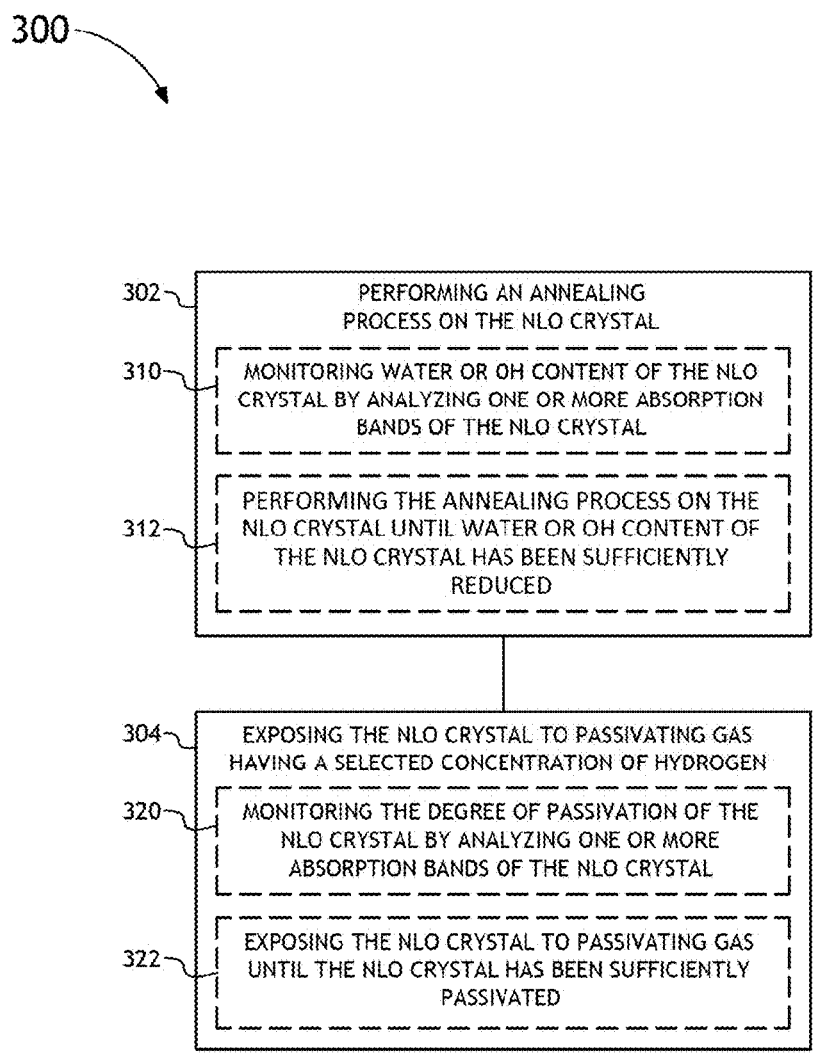
FIG. 3D is a flow diagram illustrating a method for annealing and passivating a NLO crystal, in accordance with one embodiment of the present invention.

Referring to FIGS. 3B and 3D, the annealing process of step 302 may further include a step 310 of monitoring the water or OH content of the NLO crystal by analyzing one or more absorption bands of the NLO crystal 104, wherein the absorption band is affected by a change in the number of OH bonds of the NLO crystal 104. The absorption band may be analyzed by using any method known to the art for detecting a level at which the NLO crystal 104 absorbs illumination having one or more wavelengths. For example, utilizing FTIR, the water or OH content of the NLO crystal 104 may be monitored by observing at least one absorption band in the Infrared (IR) spectrum of the NLO crystal 104. An FTIR process for monitoring the water or OH content of the NLO crystal 104 may include one or more of the following steps: (i) transmitting illumination having one or more wavelengths through the NLO crystal 104; (ii) detecting illumination transmitted through the NLO crystal 104; (iii) determining an amount of illumination absorbed by the NLO crystal 104 at one or more wavelengths utilizing information about illumination transmitted through the NLO crystal 104; and (iv) determining the water or OH content or change in water or OH content of the NLO crystal 104 utilizing a correlation between illumination absorbed by the NLO crystal 104 at one or more wavelengths and the amount or change in amount of OH bonds of the NLO crystal 104.

In a further embodiment, the annealing process of step 302 may further include a step 312 of performing one or more steps of the annealing process until a determination is made utilizing the monitoring process of step 310 that the water or OH content of the NLO crystal has been sufficiently reduced. For example, the water or OH content of the NLO crystal 104 may be determined by observing one or more absorption bands of the NLO crystal 104 appearing at one or more wavelengths of the IR spectrum in the range of approximately 3200 to 4000 $cm^{-1}$, wherein the amplitude or intensity of the absorption band appearing at the wavelength correlates to the amount or change in amount of OH bonds of the NLO crystal 104. The foregoing range of absorption band wavelengths is included by way of example only and it is contemplated that one or more absorption bands may appear at other wavelengths in the IR spectrum; accordingly, the foregoing range of wavelengths is not intended to limit the present invention in any way.

The foregoing steps of the annealing process of step 302 are neither sequential nor mandatory. The steps may occur in any order or concurrent with one another. For example, it is contemplated that the NLO crystal 104 may be maintained at the selected temperature; concurrently, the water or OH content of the NLO crystal 104 may be monitored utilizing FTIR as provided for by step 310. It is further contemplated that the temperature of the NLO crystal 104 may be maintained at the selected temperature until the water or OH content of the NLO crystal 104 has been sufficiently reduced as provided for by step 312. In some instances it may be advantageous to combine some or all of the steps and to arrange the steps in a sequence that departs from the order in which the steps have been discussed herein. The discussion herein is explanatory only and is not intended to limit the method or methods disclosed herein to any particular sequence, order, or combination of steps.

After the NLO crystal 104 has been annealed to reduce the water or OH content of the NLO crystal 104, it may be advantageous to passivate the NLO crystal 104 with hydrogen to cure crystal defects caused by one or more dangling or broken bonds, some of which may have resulted from the annealing process of step 302. Accordingly, in step 304 of the method 300 the NLO crystal 104 may be exposed to passivating gas within a container such as the exposure chamber 101 of the system 100. The passivating gas may be a gas mixture having a selected concentration of hydrogen. The hydrogen concentration may be a user selected concentration, a concentration determined utilizing one or more attributes of the NLO crystal 104, or any acceptable concentration for curing crystal defects of the NLO crystal 104 by attaching hydrogen atoms from the passivating gas to broken or dangling bonds of the NLO crystal 104. For example, in one embodiment the selected hydrogen concentration of the passivating gas may be a hydrogen concentration in the range of approximately 5 to 10% of the passivating gas mixture. However, the foregoing hydrogen concentration is only included by way of example, and it is not intended to limit the present invention in any way. In some embodiments, step 304 may further include one or more steps or elements from the method 200 of passivating the NLO crystal 104, previously discussed.

Referring to FIGS. 3C and 3D, the passivating process of step 304 may further include a step 320 of monitoring the degree of passivation of the NLO crystal 104. The degree of passivation may be monitored by analyzing one or more absorption bands of the NLO crystal 104, wherein the absorption band is affected by a change in the number of OH bonds of the NLO crystal 104. The absorption band may be analyzed by using any method known to the art for detecting a level at which the NLO crystal 104 absorbs illumination having one or more wavelengths. For example, utilizing FTIR, the degree of passivation of the NLO crystal 104 may be monitored by observing at least one absorption band in the Infrared (IR) spectrum of the NLO crystal 104. An FTIR process for monitoring the degree of passivation of the NLO crystal 104 may include one or more of the following steps: (i) transmitting illumination having one or more wavelengths through the NLO crystal 104; (ii) detecting illumination transmitted through the NLO crystal 104; (iii) determining an amount of illumination absorbed by the NLO crystal 104 at one or more wavelengths utilizing information about illumination transmitted through the NLO crystal 104; and (iv) determining the degree of passivation of the NLO crystal 104 utilizing a correlation between illumination absorbed by the NLO crystal 104 at one or more wavelengths and the amount or change in amount of OH bonds of the NLO crystal 104.

In a further embodiment, step 304 may further include a step 322 of exposing the NLO crystal 104 to passivating gas until the NLO crystal 104 is sufficiently passivated. The step 320 of monitoring the degree of passivation of the NLO crystal 104 may be utilized to determine whether or not the NLO crystal 104 has been sufficiently passivated. For example, the degree of passivation of the NLO crystal 104 may be determined by observing one or more absorption bands of the NLO crystal 104 appearing or changing intensity at one or more wavelengths of the IR spectrum in the range of approximately 3200 to 4000 $cm^{-1}$, wherein the amplitude or intensity of the absorption band appearing or changing intensity at the wavelength correlates to the amount or change in amount of OH bonds of the NLO crystal 104. The foregoing range of absorption band wavelengths is included by way of example only and it is contemplated that one or more absorption bands may appear at other wavelengths in the IR spectrum; accordingly, the foregoing range of wavelengths is not intended to limit the present invention in any way.

The foregoing steps are neither sequential nor mandatory and may occur in any order or concurrent with one another. For example, it is contemplated that in one embodiment of step 304, the NLO crystal 104 may be exposed to passivating gas having the selected concentration of hydrogen; and concurrently, the degree of passivation of the NLO crystal 104 may be monitored utilizing FTIR as provided for in step 320. It is further contemplated that the NLO crystal may be exposed to passivating gas until the NLO crystal 104 has been sufficiently passivated as provided for in step 322, wherein the monitoring technique of step 320 may be utilized to determine whether or not the NLO crystal 104 has been sufficiently passivated. In some instances it may be advantageous to combine some or all of the steps and to arrange the steps in a sequence that departs from the order in which the steps have been discussed herein. The discussion herein is explanatory only and is not intended to limit the method or methods disclosed herein to any particular sequence, order, or combination of steps.

It may be advantageous to incorporate the NLO crystal 104, having been sufficiently annealed and passivated, into a laser system for better physical/optical performance or greater crystal lifetime than could be achieved utilizing an unmodified NLO crystal 104. The laser system configuration of the present disclosure may include, but is not limited to, configurations such as mode-locked, CW, Q-switched, and any other laser or laser system including one or more nonlinear crystals. The description herein is further intended to include a broad range of possible laser spectra, including but not limited to electromagnetic spectra such as Deep Ultraviolet (DUV), Ultraviolet (UV), Infrared, visible, and the like. As used herein, the terms "laser system" and "laser" may be used interchangeably to describe a configuration of one or more lasers.

Figure 4:
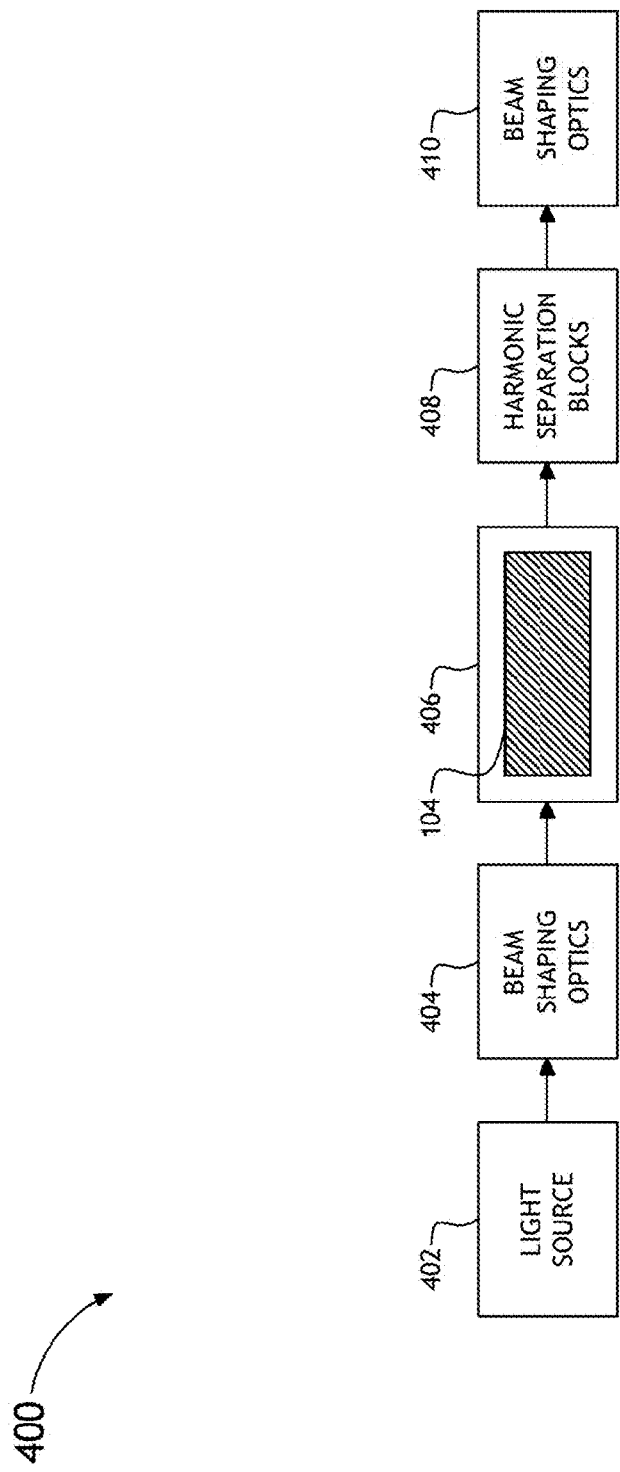
FIG. 4 is a block diagram illustrating a laser system equipped with an annealed and passivated NLO crystal, in accordance with one embodiment of the present invention.

FIG. 4 illustrates a laser system 400 equipped with a passivated and/or annealed NLO crystal 104. The laser system 400 of the present invention may include, but is not limited to, a light source 402, a first set of beam shaping optics 404, the passivated/annealed crystal 104 as described previously herein, a housing unit 406, a set of harmonic separation elements 408, and a second set of beam shaping optics 410.

In one aspect, the output of a light source 402 may be focused to an elliptical cross-section Gaussian beam waist in or proximate to a passivated/annealed NLO crystal 104 using beam shaping optics 404. As used herein, the term "proximate to" is preferably less than half of the Rayleigh range from the center of crystal 104. In one embodiment, the aspect ratio between the Gaussian widths of the principle axes of the ellipse may fall between about 2:1 and about 6:1. In other embodiments the ratio between the principle axes of the ellipse may be between about 2:1 and about 10:1. In one embodiment, the wider Gaussian width is substantially aligned with the walk-off direction of the NLO crystal 104 (e.g. to within about 10° of alignment).

In another aspect, the housing unit 406 may protect the NLO crystal 104 from ambient atmospheric conditions and other impurities, thereby facilitating maintenance of its passivated/annealed condition. Note that a crystal exposed to atmospheric water and other impurities over time will begin to deteriorate and may revert back to an unpassivated or un-annealed state. Crystal housing units are described generally in U.S. patent application Ser. No. 12/154,337, entitled "Enclosure For Controlling The Environment of Optical Crystals", filed May 6, 2008, which is incorporated herein by reference in the entirety. In some embodiments, housing unit 406 may include a large structure suitable for housing crystal 104 and other components of the laser system 400. In other embodiments, housing 406 may be large enough to house all components of the laser system 400. Note that the larger the housing, the more precautions needed for maintenance and repair of the laser system (to protect crystal 104 from degradation and maintain its passivated/annealed condition). As such, in further aspects, the housing unit 406 may consist of a small housing structure suitable for enclosing primarily only the NLO crystal 104.

Beam shaping optics 404 may include anamorphic optics, which may change the cross section of output from light source 402. Anamorphic optics may include, for example, at least one of a prism, a cylindrical curvature element, a radially-symmetric curvature element, and a diffractive element. In one embodiment, light source 402 may include a laser producing a frequency in the visible range (e.g. 532 nm) to be doubled inside crystal 104. In other embodiments, light source 402 may include a laser source producing two or more frequencies to be combined inside crystal 104 to generate a sum or difference frequency. Frequency conversion and associated optics and hardware are described Dribinski et al. in U.S. patent application Ser. No. 13/412,564, filed on Mar. 6, 2012, which is incorporated herein by reference in the entirety.

Figure 5:
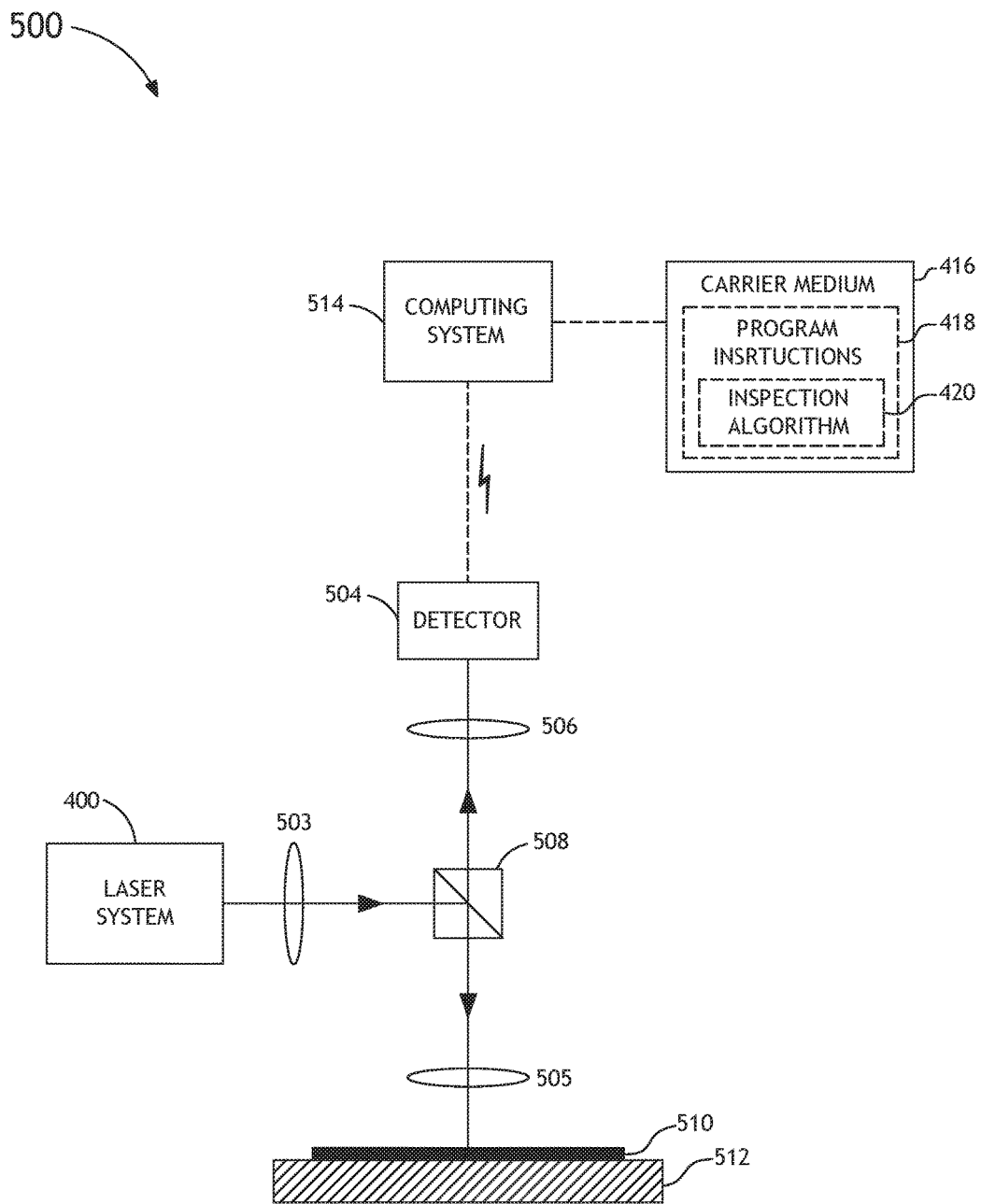
FIG. 5 is a block diagram illustrating a system for inspecting a wafer or a photomask, in accordance with one embodiment of the present invention.

FIG. 5 illustrates an inspection system 500 configured for measuring or analyzing defects of one or more samples 510, such as a photomask (i.e., a reticle), wafer, or any other sample that may be analyzed utilizing an optical inspection system. The inspection system 500 may include a laser system 400 as described above. The laser system 400 may include one or more of the passivated/annealed NLO crystals 104 described throughout the present disclosure. In one embodiment, the NLO crystal 104 of the laser system 400 may be sufficiently annealed to reduce the water content of the NLO crystal 104 to a selected water content level.

In a further embodiment, the NLO crystal 104 of the laser system 400 may be sufficiently passivated to cure crystal defects caused by dangling or broken bonds, such as dangling oxygen bonds. Dangling or broken bonds of the NLO crystal 104 may be cured through passivation by bonding hydrogen atoms to the broken or dangling bonds of the NLO crystal 104. In some cases, a portion of dangling or broken bonds may be products of the annealing process performed on the NLO crystal 104. The NLO crystal 104 may be passivated to a selected degree of passivation that is acceptable for achieving desired physical/optical performance, improved LID resistance, improved output beam quality, improved output stability, increased crystal lifetime, or higher operating power.

The NLO crystal 104 of the laser system 400 may have at least one absorption band in the IR spectrum of the NLO crystal 104 correlated to the presence, absence, or amount of OH bonds of the NLO crystal 104. The absorption band of the NLO crystal 104 may be measured utilizing FTIR to determine the degree of passivation or the water content level of the NLO crystal 104. A specified amplitude or intensity of the absorption band of the NLO crystal 104 may correspond to the sufficient annealing level or the sufficient passivating level of the NLO crystal 104. The specified amplitude or intensity of the absorption band may be a user selected value, or a value determined utilizing one or more attributes of the NLO crystal 104. Accordingly, the absorption band of NLO crystal 104 of the laser system 400 may have an amplitude or intensity at or near the specified amplitude or intensity. The laser system 400 may further include at least one electromagnetic source, such as a diode pumped solid state (DPSS) source or a fiber IR source, configured to provide illumination to the NLO crystal 104. At least a portion of the illumination provided by the electromagnetic source may be directly or indirectly transmitted through the NLO crystal 104 in a frequency conversion process of the crystal 104.

The inspection system 500 may further include a sample stage 512 configured to hold the sample 510 during the inspection process. The sample stage 512 may be configured to hold the sample 510 in a location where the sample 510 may receive at least a portion of illumination transmitted from the laser system 400. The sample stage 512 may be further configured to actuate the sample 510 to a user selected location. The sample stage 512 may further be communicatively coupled to one or more computing systems and configured to actuate the sample 510 to the user selected location or to a location determined by the computing system, wherein the sample 510 may receive at least a portion of illumination transmitted from the laser system 400.

The inspection system 500 may further include a detector 504 configured to directly or indirectly receive at least a portion of illumination reflected from a surface of the sample 510. The detector 504 may include any suitable detector known to the art, such as a charged coupled device (CCD) or a time-delay-and- integration (TDI) CCD based detector. The inspection system 500 may further include one or more computing systems 514 communicatively coupled to the detector 504. The computing system 514 may be configured to receive information regarding characteristics of illumination reflected from the surface of the sample 510 from the detector 504. The computing system 514 may be further configured to execute an inspection algorithm from program instructions 418 on a carrier medium 416. The inspection algorithm 420 may be any inspection algorithm known to the art for measuring one or more defects of the sample 510 utilizing information regarding characteristics of illumination reflected from the surface of the sample 510. Accordingly, the computing system 514 may utilize information regarding illumination reflected from the surface of the sample 510 to make measurements, such as presence, absence, quantity, and/or type of defects of the sample 510.

The inspection system 500 may include one or more illumination optical elements 503 (e.g. retarders, quarter wave plates, focus optics, phase modulators, polarizers, mirrors, beam splitters, reflectors, converging/diverging lenses, prisms, etc.). The illumination optical elements 503 may be configured to directly or indirectly receive illumination emanating from the laser system 400. The illumination optical elements 503 may be further configured to transmit and/or direct at least a portion of illumination directly or indirectly received from the laser system 400 along an illumination path of the inspection system 500 to the surface of the sample 510. The illumination path may be any path along which illumination can travel from the laser system 400 to the surface of the sample 510, such as a direct line of sight between the laser system 400 and the surface of the sample 510. In some embodiments, the illumination path may be a path delineated by a configuration of one or more optical elements including, but not limited to, the illumination optical elements or any other optical elements disclosed herein.

In one embodiment, the illumination path of the inspection system 500 may include a beam splitter 508 configured to transmit at least a portion of illumination received directly or indirectly from the laser system 400 to the surface of the sample 510 or to a further component of the illumination path. The beam splitter 508 may be any optical device capable of splitting a beam of illumination into two or more beams of illumination. The illumination path may further include inspection optical elements 505 (e.g., retarders, quarter wave plates, focus optics, phase modulators, polarizers, mirrors, beam splitters, reflectors, converging/diverging lenses, prisms, etc.) configured to transmit at least a portion of illumination received directly or indirectly from the laser system 400 to the surface of the sample 510.

In one embodiment the inspection system 500 may include collection optical elements 506 (e.g. retarders, quarter wave plates, focus optics, phase modulators, polarizers, mirrors, beam splitters, reflectors, converging/diverging lenses, prisms, etc.) configured to directly or indirectly receive at least a portion of illumination reflected from the surface of the sample 510. The collection optical elements 506 may be further configured to transmit at least a portion of illumination directly or indirectly received from the surface of the sample 510 along a collection path of the inspection system 500 to the detector 504. The collection path may be any path along which illumination can travel from the surface of the sample 510 to the detector 504, such as a direct line of sight between the surface of the sample 510 and the detector 504. In some embodiments, the collection path may be a path delineated by a configuration of one or more optical elements including, but not limited to, the collection optical elements 506 or any other optical elements disclosed herein.

While the present disclosure describes the inspection system 500 in the context of generically inspecting one or more samples, it is contemplated that the inventive aspects of the inspection system 500 may be extended to wide array of inspection or metrology systems utilized in the fabrication or analysis of semiconductors or semiconductor components. The inspection system 500 may be configured for one or more modes of operation known to the art. For example, the inspection system 500 may be configured for bright-field inspection, dark-field inspection, or any other mode or configuration now or hereafter known to the art. The inspection system 500 may be further configured for one or more inspection capabilities known to the art. For example, the inspection system 500 may be configured for inspecting one or more photomasks, patterned wafers, unpatterned wafers, or any other inspection capability now or hereafter known to the art.

It should be recognized that the various steps described throughout the present disclosure may be carried out by a single computing system or, alternatively, a multiple computing system. Moreover, different subsystems of the system may include a computing system suitable for carrying out at least a portion of the steps described above. Therefore, the above description should not be interpreted as a limitation on the present invention but merely an illustration. Further, the one or more computing systems may be configured to perform any other step(s) of any of the method embodiments described herein.

The computing system may include, but is not limited to, a personal computing system, mainframe computing system, workstation, image computer, parallel processor, or any other device known in the art. In general, the term "computing system" may be broadly defined to encompass any device having one or more processors, which execute instructions from a memory medium.

Program instructions implementing methods such as those described herein may be transmitted over or stored on carrier medium. The carrier medium may be a transmission medium such as a wire, cable, or wireless transmission link. The carrier medium may also include a storage medium such as a read-only memory, a random access memory, a magnetic or optical disk, or a magnetic tape.

All of the methods described herein may include storing results of one or more steps of the method embodiments in a storage medium. The results may include any of the results described herein and may be stored in any manner known in the art. The storage medium may include any storage medium described herein or any other suitable storage medium known in the art. After the results have been stored, the results can be accessed in the storage medium and used by any of the method or system embodiments described herein, formatted for display to a user, used by another software module, method, or system, etc. Furthermore, the results may be stored "permanently," "semi-permanently," temporarily, or for some period of time. For example, the storage medium may be random access memory (RAM), and the results may not necessarily persist indefinitely in the storage medium.

It is further contemplated that each of the embodiments of the method described above may include any other step(s) of any other method(s) described herein. In addition, each of the embodiments of the method described above may be performed by any of the systems described herein.

Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "connected", or "coupled", to each other to achieve the desired functionality, and any two components capable of being so associated can also be viewed as being "couplable", to each other to achieve the desired functionality. Specific examples of couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein.

Furthermore, it is to be understood that the invention is defined by the appended claims.

Although particular embodiments of this invention have been illustrated, it is apparent that various modifications and embodiments of the invention may be made by those skilled in the art without departing from the scope and spirit of the foregoing disclosure. Accordingly, the scope of the invention should be limited only by the claims appended hereto.

It is believed that the present disclosure and many of its attendant advantages will be understood by the foregoing description, and it will be apparent that various changes may be made in the form, construction and arrangement of the components without departing from the disclosed subject matter or without sacrificing all of its material advantages. The form described is merely explanatory, and it is the intention of the following claims to encompass and include such changes.

What is claimed:

1. A laser system comprising:
   an annealed and passivated nonlinear optical (NLO) crystal comprising cesium lithium borate, the annealed and passivated NLO crystal annealed within a selected temperature range and passivated with at least one of hydrogen, deuterium, a hydrogen-containing compound or a deuterium-containing compound to a selected passivation level;
   at least one light source configured to generate light of a selected wavelength, the light source further configured to transmit light through the NLO crystal, wherein the NLO crystal emits deep ultraviolet light in response to the light from the light source; and
   a crystal housing unit configured to house the NLO crystal.

2. The system of claim 1, wherein the at least one light source emits light at a first wavelength.

3. The system of claim 2, wherein the NLO emits light at a second wavelength, wherein the second wavelength is approximately one-half the first wavelength.

4. The system of claim 1, wherein the at least one light source comprises:
   at least one laser having at least one diode pumped solid state (DPSS) source.

5. The system of claim 1, wherein the at least one light source comprises:
   at least one laser having at least one fiber IR source.

6. The system of claim 1, wherein at least one of dangling bonds or broken bonds are repaired within the NLO crystal with the passivating gas.

7. The system of claim 1, wherein the passivating gas comprises:
   a mixture of hydrogen, deuterium and an inert gas.

8. The system of claim 1, wherein the passivating gas comprises:
   at least one inert gas mixed with at least one of hydrogen, deuterium, a hydrogen-containing compound or a deuterium-containing compound.

9. The system of claim 1, wherein the NLO crystal is annealed at a temperature between room temperature and a melting point of the NLO crystal.

10. The system of claim 9, wherein the NLO crystal is annealed at a temperature between 300° C. and 350° C.

11. The system of claim 1, further comprising:
    a set of beam shaping optics.

12. The system of claim 11, wherein the set of beam shaping optics are configured to focus an output of the at least one light source into the NLO crystal.

13. The system of claim 12, wherein the set of beam shaping optics are configured to focus the output of the at least one light source into an elliptical cross-section Gaussian beam waist within the NLO crystal.

14. The system of claim 11, wherein the set of beam shaping optics comprise:
    one or more anamorphic optics.

15. An apparatus comprising: a nonlinear optical crystal comprising cesium lithium borate, wherein the NLO crystal is annealed within a selected temperature range, the NLO crystal passivated with at least one of hydrogen, deuterium, a hydrogen-containing compound or a deuterium-containing compound to a selected passivation level, wherein the NLO crystal emits deep ultraviolet light in response to light from a light source.

* * * * *